(12) United States Patent
Kilcher et al.

(10) Patent No.: US 7,331,788 B2
(45) Date of Patent: Feb. 19, 2008

(54) CLAMPING CORD WITH POLYMERIC WEDGE COMPONENT, AND METHOD OF AFFIXATION

(75) Inventors: Beat Kilcher, Bosco Luganese (CH); Marco Da Rold, Odogno (CH)

(73) Assignee: KerrHawe SA (CH)

( * ) Notice: Subject to any disclaimer, the term of this patent is extended or adjusted under 35 U.S.C. 154(b) by 130 days.

(21) Appl. No.: 11/013,615

(22) Filed: Dec. 16, 2004

(65) Prior Publication Data

US 2006/0134579 A1 Jun. 22, 2006

(51) Int. Cl.
*A61C 5/14* (2006.01)
*A61C 15/00* (2006.01)
(52) U.S. Cl. ........................ 433/136; 132/329
(58) Field of Classification Search ............... 132/329, 132/321; 433/149, 136
See application file for complete search history.

(56) References Cited

U.S. PATENT DOCUMENTS

| | | | |
|---|---|---|---|
| 3,838,702 A * | 10/1974 | Standish et al. ............ 132/321 |
| 3,896,824 A | 7/1975 | Thornton |
| 3,943,949 A | 3/1976 | Ashton et al. |
| 4,008,727 A | 2/1977 | Thornton |
| 4,198,977 A | 4/1980 | Aoki |
| 4,465,462 A | 8/1984 | Ticknor |
| 4,832,063 A | 5/1989 | Smole |
| 5,063,948 A | 11/1991 | Lloyd |
| 5,104,317 A | 4/1992 | Riazi |
| 5,311,890 A | 5/1994 | Thornton |
| 5,316,028 A | 5/1994 | Flemming |
| 5,353,820 A | 10/1994 | Suhonen et al. |
| 5,392,794 A | 2/1995 | Striebel |
| 5,433,226 A | 7/1995 | Burch |
| 5,505,216 A | 4/1996 | Gilligan et al. |
| 5,540,588 A | 7/1996 | Earle |
| 5,558,901 A | 9/1996 | Gilligan et al. |
| 5,566,691 A | 10/1996 | Dolan et al. |
| 5,743,738 A | 4/1998 | Baffelli et al. |
| 5,755,243 A | 5/1998 | Roberts et al. |
| 5,878,758 A | 3/1999 | Bacino et al. |
| 5,890,500 A | 4/1999 | Mabon et al. |
| 6,003,525 A | 12/1999 | Katz |
| 6,027,592 A | 2/2000 | Tseng et al. |
| 6,029,678 A | 2/2000 | Tsao et al. |
| 6,039,054 A | 3/2000 | Park et al. |
| 6,644,323 B1 | 11/2003 | Clark |
| 6,761,562 B2 | 7/2004 | Von Weissenfluh |

FOREIGN PATENT DOCUMENTS

WO  WO 99/29257  6/1999
WO  WO 2004/034922  4/2004

OTHER PUBLICATIONS

European Patent Office, Partial European Search Report, corresponding EP application No. 05257607.1, mailed Mar. 9, 2006.

\* cited by examiner

*Primary Examiner*—Cris Rodriguez
*Assistant Examiner*—Candice C Stokes
(74) *Attorney, Agent, or Firm*—Wood, Herron & Evans

(57) ABSTRACT

The present invention relates to the affixation of dental dams and Class III matrixes utilized in conservative dentistry and oral surgery. In particular, the present invention relates to a device and method for retaining and stabilizing a dental dam or Class III matrix, or other device, in the mouth of the patient, which can be clamped between 2 adjacent teeth.

18 Claims, 4 Drawing Sheets

CLAMPING CORD WITH POLYMERIC WEDGE COMPONENT, AND METHOD OF AFFIXATION

FIELD OF THE INVENTION

The present invention relates to the affixation of dental dams and Class III matrixes utilized in conservative dentistry and oral surgery. In particular, the present invention relates to a device and method for retaining and stabilizing a dental dam or Class III matrix, or other device, in the mouth of a patient, which can be clamped between 2 adjacent teeth.

BACKGROUND OF THE INVENTION

Dental dams and Class III matrices, e.g. a mylar foil, are commonly used in oral surgery and conservative dentistry. The use of the dental dam, or Class III matrix, isolates the teeth or tooth being treated from other tissues in the mouth and throat. The dam, comprised of a thin flexible piece of elastomeric material, is typically manufactured from a latex material, though alternatively it can be manufactured from silicone or nitrile rubber.

The dental dam improves the efficiency of the dental operation by assuring a dry working area during all steps of the operation. Further, the dentist or oral surgeon is protected from infectious disease that may reside in the mouth or throat of the patient.

The dental dam is secured in place by first fitting the dam to a rubber dam frame, which is positioned over the face and is dimensionally larger than the opened mouth to allow the dentist or oral surgeon ready access to the tooth or teeth requiring attention. Holes are then punched in the dam corresponding to the teeth that will be exposed through the dam. Alternatively, the dam is first punched to expose the teeth, and thereafter the edges of the dam are affixed to the rubber dam frame.

Once the dam is positioned to expose the teeth, it must be stabilized from movement during treatment by the dentist or oral surgeon by some type of retaining system. Previously, a retainer clamp was used to stabilize the dental dam. This clamp consists of four prongs and two jaws connected by a bow. Stabilization using this clamp is optimized if the clamp is configured to a specific tooth within a narrowed tolerance range. Failure to closely match the retainer clamp to the tooth tends to permit slippage or unwanted movement of the dam during the surgical or conservative procedure. This movement may also result in formation of an inferior seal around the teeth that causes fluid to drain into the area being treated.

For these and other reasons, it would be desirable to provide a retaining device that addresses these and other deficiencies encountered in stabilizing the dental dam, as well as providing a method for retaining a dental dam, or Class III matrix, which is neither complicated nor causes iatrogenic damage.

SUMMARY OF THE INVENTION

In one embodiment of the present invention, a dental or clamping cord includes a core portion and a clamping portion. The core portion is of a first diameter and includes longitudinally arranged fibers. The clamping portion is of a second diameter greater than the first and includes a section of the fibers arranged longitudinally along and outward of the core portion, these fibers having interstices therebetween. The clamping portion further includes a polymeric material that surrounds the outwardly arranged fibers and substantially fills the interstices therebetween. The resulting clamping cord is so configured to permit the core portion of a first diameter to be inserted or slipped through a contact point between two adjacent teeth and pulled, or slid, therethrough whereby the greater second diameter of the clamping cord is of sufficient diameter to become lodged in the space between the two adjacent teeth.

In another aspect of the invention, a method is provided for retaining a dental dam positioned over and around teeth in the mouth of a patient by selecting a length of the core portion of the dental or clamping cord, inserting the core portion in a space between at least two adjacent teeth, and moving the clamping cord axially through the space until the clamping portion becomes lodged in the space or spaces between adjacent teeth. The core portion also may be used to facilitate placement of the dental dam around the teeth, whereby the core portion is slipped between adjacent teeth and forced against a surface of the dental dam so that the teeth may be received through corresponding openings in the dental dam.

In another embodiment, a Class III matrix likewise can be affixed in place by inserting the clamping cord between the tooth receiving the Class III matrix and an adjacent tooth, and thereafter pulling the clamping cord axially through the space between these two teeth until the larger diameter clamping portion of the clamping cord wedges the Class III matrix into position. In an exemplary embodiment, the clamping cord includes an optional palatinal stopper attached to, or integrated with, an end of the clamping portion. In practice, after insertion of the clamping cord, the clamping portion is moved between the adjacent teeth until the palatinal stopper abuts against the Class III matrix, wherein the stopper is pressed against the palatinal teeth surfaces. When the clamping cord wedges between the teeth, the palatinal stopper helps hold the Class III matrix in position, such as for filling a cavity.

In connection with the method of either retaining a dental dam, or a Class III matrix, the clamping cord can be cut a short distance from the point of wedging between adjacent teeth. This will not adversely affect the quality of the stabilization of either the dental dam or the Class III matrix, but will provide fewer obstructions for the dentist or oral surgeon during the treatment procedure.

By virtue of the foregoing, there is provided an improved clamping cord that may be inserted through or between at least two adjacent teeth and thereby, after wedging between the teeth, serves to effectively stabilize a dental dam or Class III matrix position.

BRIEF DESCRIPTION OF THE DRAWING

The accompanying drawings, which are incorporated in and constitute a part of this specification, illustrate an embodiment of the invention and, together with the general description of the invention given above, and detailed description given below, serve to explain the invention.

DETAILED DESCRIPTION OF THE INVENTION

Figure 1:
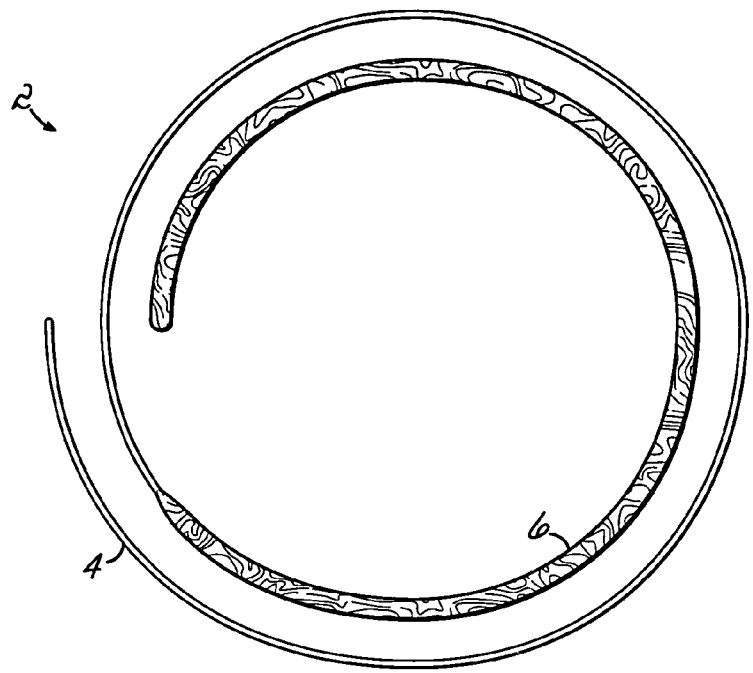
FIG. 1 is an overhead view of the clamping cord depicting the smaller diameter core portion and larger diameter clamping portion.

With reference to FIG. 1, the clamping cord 2 of the present invention includes a core portion 4 and a clamping portion 6. Optionally, the clamping cord 2 may have a section of core portion 4 extending from both ends of clamping portion 6, thereby permitting introduction of the clamping cord 2 between multiple sets of teeth.

Figure 2:
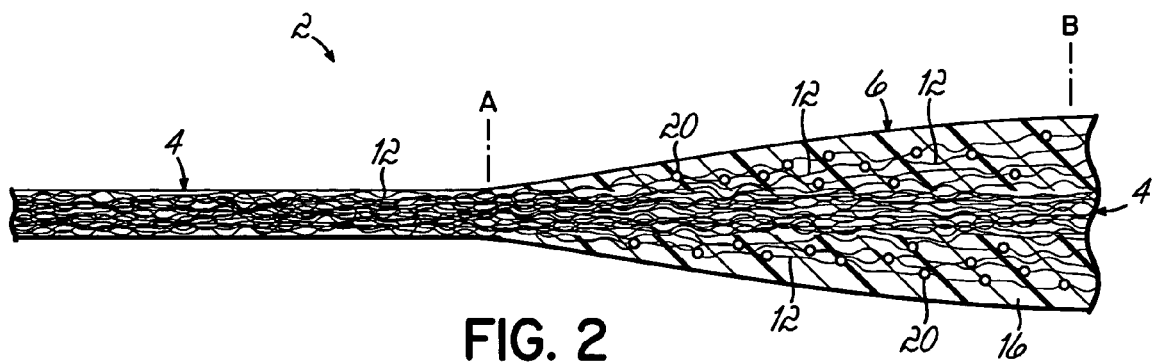
FIG. 2 is a cut-away side view of the clamping cord depicting the smaller diameter core portion, transitioning to the larger diameter clamping portion.

FIG. 2 depicts the clamping cord 2 in cross-section, showing the core portion 4 in the depicted embodiment having longitudinally arranged fibers 12, which extend the length of the clamping cord 2. The longitudinally arranged fibers 12 may be round or flat, natural or synthetic, and may be coated with a wax, polytetrafluoroethylene (PTFE), or other suitable lubricant commonly known in the art, unless the treatment process for the clamping portion 6, as described below, would be adversely affected by such a coating. The fibers 12 may include nylon, polyester, polypropylene, natural fibers like cotton, or other materials capable to impart tensile strength. The core portion 4 of the clamping cord 2 is shown as being circular, or round, in shape but also may include other configurations, such as polygonal, and preferably includes a diameter, or width, of about 0.1 to 0.5 mm.

The clamping portion 6 transitions from the core portion 4 at point A and increases in diameter to a generally maximum diameter at point B thereon. The clamping portion 6 similarly is shown as being circular, or round, in shape but also may include other configurations, such as polygonal, and preferably includes a diameter, or width, of about 0.5 mm up to a maximum of about 5 mm. Alternatively, the clamping portion 6 may present some variability in maximum diameter along its length.

The clamping portion 6 includes longitudinally arranged fibers 12 disposed outwardly of the core portion 4. In an exemplary embodiment, the longitudinally arranged fibers 12 are originally part of the core portion 4 prior to treatment involving an air jet or brush. This treatment opens the original tightly arranged fibers to create a fibrous portion outward of an untreated core portion 4 with fibers 12 having expanded volume interstices therebetween longitudinally arranged outward of the core portion 4 but still physically connected to the core portion 4. Alternatively, longitudinally arranged fibers 12 can be arranged over a section of the core portion 4 in a separate procedure, for example, as a sleeve (not shown). In this alternative embodiment, it is preferred that some type of anchoring be effected between this outwardly applied sleeve of longitudinally arranged fibers 12 and the core portion 4 to minimize axially resiliency.

The remainder of the clamping portion 6 is comprised of a polymeric elastic material 16 such as silicones, thermoplastic elastomers, or polyurethanes (PUR) that is applied onto the longitudinally arranged fibers 12 disposed outwardly of the core portion 4 to substantially impregnate the interstices thereof, following by a curing or other setting step. The polymeric elastic material 16 exhibits relatively low axially resiliency due to the existence of a plurality of axial anchoring points 20 which serve to substantially prevent movement of the polymeric elastic material 16 relative to the longitudinally arranged fibers 12. The clamping portion 6 of the clamping cord 2 preferably includes a hardness of about 10 to 90 Shore A.

The polymeric elastic material 16 in one embodiment is medical grade silicone. Alternatively, other polymeric materials can be used, such as but not limited to thermoplastic elastomers like Santoprene® available from ExxonMobil Chemical, Dynaflex® available from GLS Corporation, Pebax® available from Arkema, or polyurethane Pellethane® available from Dow Chemical, etc. In addition, the polymeric material may be colored and/or contain one or more additives to reduce friction.

Figure 5A:
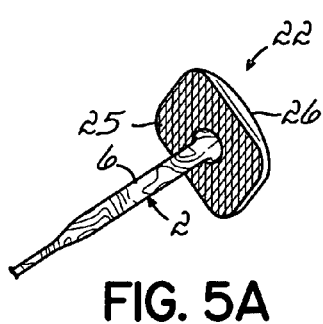
FIGS. 5A and 5B are cut-away side perspective views of another embodiment of the clamping cord of the present invention showing a palatinal stopper associated with an end of the clamping portion.
Figure 5B:
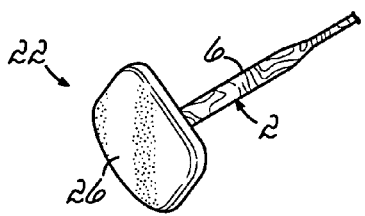

In an alternative embodiment, the clamping cord 2 incorporates a palatinal shaper 22, as depicted in FIGS. 5A and 5B. The clamping cord 2, at an end of the clamping portion 6, has affixed thereto a palatinal stopper 22, comprised in turn of a net component 25 and a polymeric-shaped component 26. The net component 25 is fibrous and preferably of the same or compatible composition to the fibers 12 of the core portion 4. As an alternative, ductile metallic or plastic fibers can be utilized to produce the net component 25 such as by being inserted between the polymeric-shaped component 26 and the end of the clamping portion 6. To minimize radial resiliency, the fibers of the net component 25 preferably are anchored to fibers 12 either in the core portion 4, the clamping portion 6, or both, prior to the incorporation of the polymeric elastic material 16. The polymeric-shaped component 26 is preferably of the same or compatible composition to the polymeric elastic material 16. As indicated above, the clamping portion 6, as shown in FIGS. 5A and 5B, may present some variability in diameter along its length, i.e. is at a lesser diameter proximal the core portion 4 than proximal the palatinal stopper 22, for use with Class III cavity application, as further explained below.

Figure 3A:
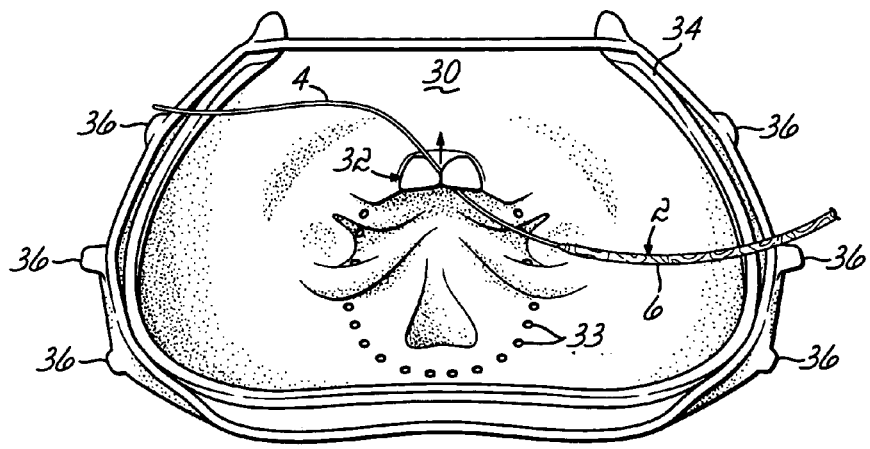
FIGS. 3A-3D diagrammatically depict the steps of pushing the dam between two teeth using the core portion of the clamping cord, and then inserting, pulling and wedging the clamping cord between two adjacent teeth in a mouth fitted with a dental dam and rubber dam frame holder.

Referring to FIGS. 3A-3E, dental dam 30 is depicted being fitted over teeth 32 by use of the core portion 4 of the clamping cord 2, and thereafter secured about the teeth 32 by use of the clamping portion 6 of the clamping cord 2. In practice, as best shown in FIG. 3A, a rubber dam frame holder 34 is arranged outward of the opened mouth, and receives the outer dimension of the dental dam 30 over retaining points 36. The core portion 4 of the clamping cord 2 can be inserted between any adjacent teeth in the mouth, and against the dental dam 30, which has openings 33 adapted to fit around the teeth 32. The core portion 6 can then be forced upwards against the dental dam 30 so that the teeth 32 may be received through the openings 33.

Figure 3B:
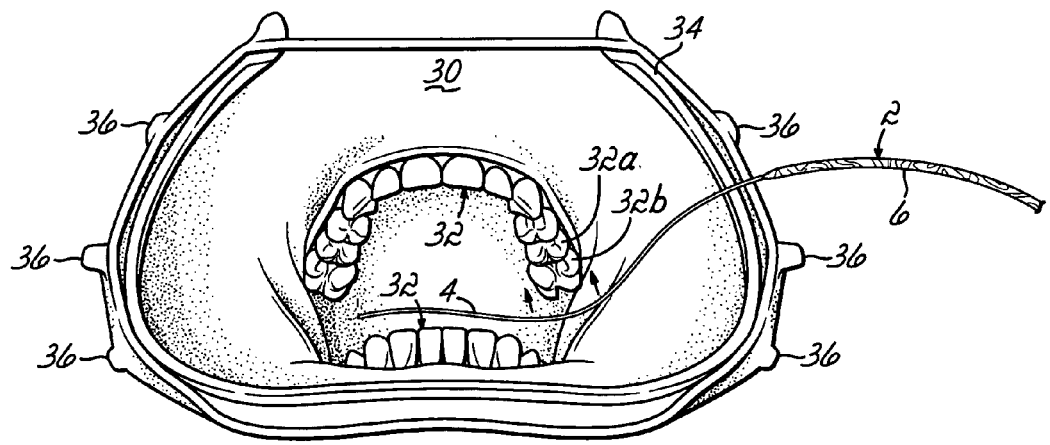
Figure 3C:
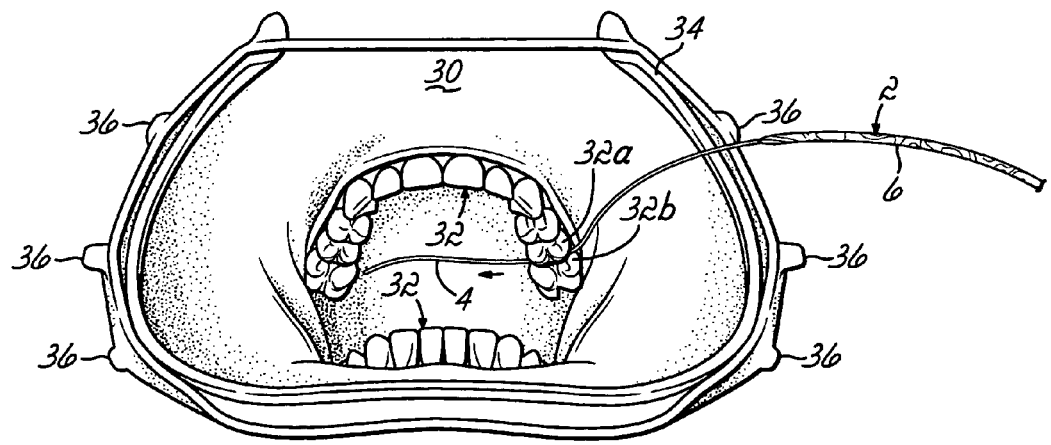
Figure 3D:
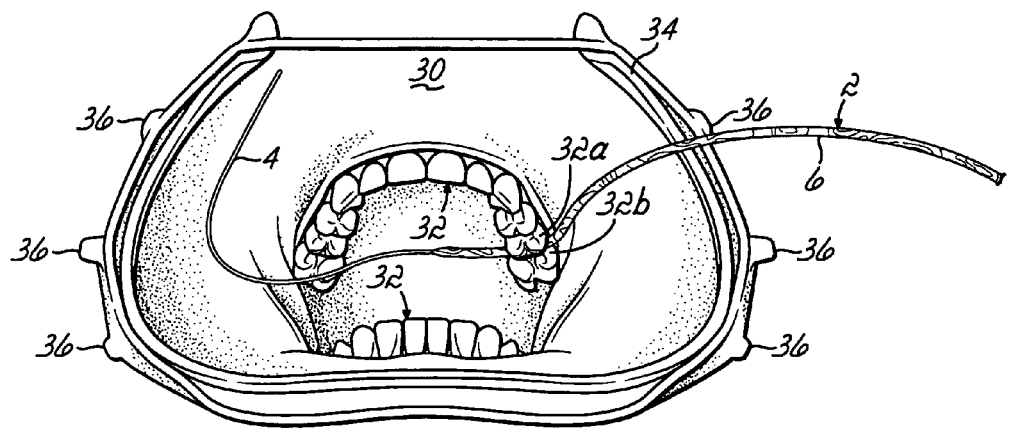

As best shown in FIGS. 3B and 3C, to prevent movement of the dental dam 30 downward over the teeth 32 after the dental dam 30 is in place, the core portion 4 of clamping cord 2 is brought into position, such as between two teeth 32a and 32b. The teeth 32a, 32b through which the core portion 4 of the clamping cord 2 is passed are upper molars 32a, 32b, i.e. the second premolar and first molar. After the core portion 4 has been inserted between the adjacent teeth 32a, 32b, the core portion 4 is pulled through the space between the two teeth 32a, 32b to eventually provide a wedging effect facilitated by the clamping portion 6 as shown in FIG. 3D. The selection of which teeth to pass the clamping cord 2 therebetween is at the discretion of the dentist or oral surgeon, and is a function of the particular tooth or teeth subject to treatment, as well as the ease in maintaining the stability of the dental dam relative to the treatment area. Because of the low axial resiliency of clamping cord 2, the clamping portion 6 can be drawn as far as desired by the dentist or oral surgeon through the space between teeth 32a, 32b as is necessary to effectively stabilize the dental dam 30.

Figure 3E:
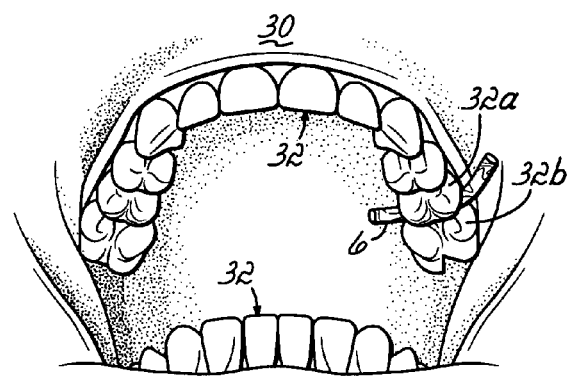
FIG. 3E is a diagrammatic depiction showing the clamping cord wedged between two adjacent teeth and cut to minimize obstructions in the treatment area.

With further reference to FIG. 3E, that portion of the clamping cord 2 located more than a few millimeters outward of the space between teeth 32a, 32b is cut. The resultant wedge created by the clamping portion 6 is minimally obtrusive to the dentist or oral surgeon performing a treatment procedure, and the relatively high radial resiliency of the polymeric elastic material 16 allows for a secure wedging operation, thereby preventing movement of the remaining portion of the clamping cord 2 during the treatment procedure.

Figure 4:
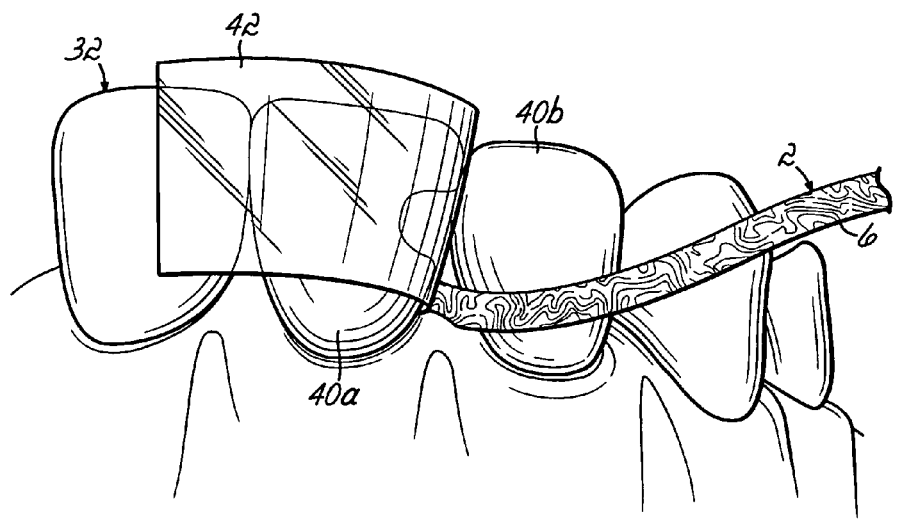
FIG. 4 is a diagrammatic depiction of the use of the clamping portion of the clamping cord pulled between two adjacent teeth, one tooth being fitted with a Class III matrix.

FIG. 4 depicts a tooth 40A fitted with a Class III matrix 42, i.e. a mylar foil, for use with a Class III cavity application, and the clamping portion 6 of the clamping cord 2 having been inserted and pulled between the Class III matrix 42 and adjacent tooth 40b with the larger diameter clamping portion 6 wedging the Class III matrix 42 into position. As indicated above, it should be understood that the clamping portion 6 may present some variability in diameter along its length (See FIGS. 5A and 5B), which may permit easier initial wedging of the clamping portion 6 between teeth 40a and 40b as well as minimize patient discomfort in the instance an anesthetic is not permitted or utilized, such as for Class III cavity application, as represented by FIG. 4.

Figure 6A:
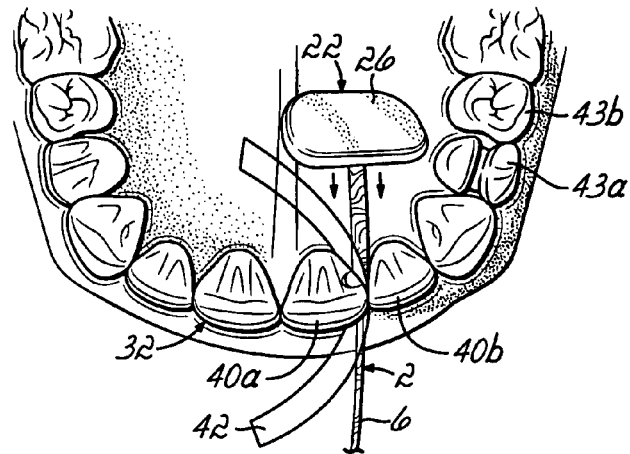
FIGS. 6A-6C diagrammatically depict the use of the clamping cord of FIGS. 5A and 5B inserted, pulled, and secured between two adjacent teeth, in an alternative procedure for stabilizing a Class III matrix.
Figure 6B:
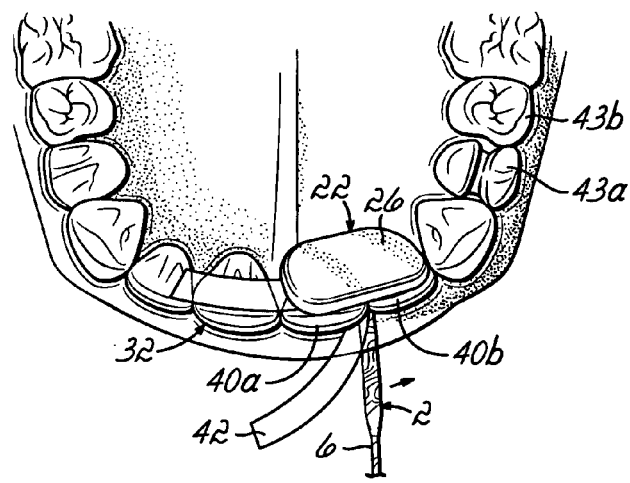
Figure 6C:
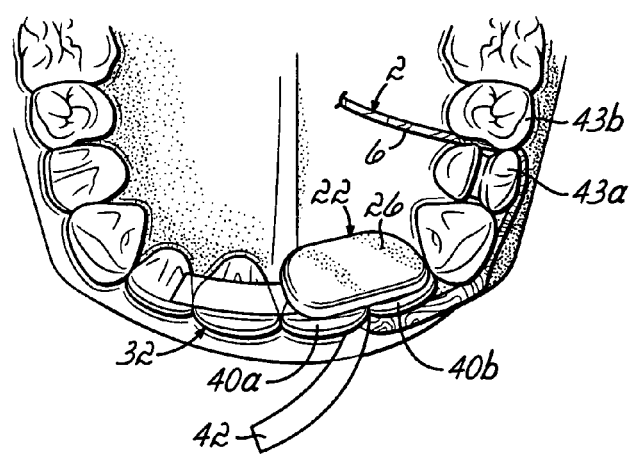

In an alternative embodiment, FIGS. 6A-6C depict the tooth 40a fitted with the Class III matrix 42, i.e. the mylar foil, and the clamping cord 2 having incorporated therein the palatinal shaper 22, as depicted in FIGS. 5A and 5B. In this series, clamping portion 6 of the clamping cord 2 is pulled between the Class III matrix 42 and adjacent tooth 40b until the palatinal stopper 22 abuts against the Class III matrix 42, wherein the stopper 22 is pressed and adapted anatomically against the palatinal teeth surfaces with the larger diameter clamping portion 6 wedging the Class III matrix 42 into position. In addition, the clamping portion 6 of the clamping cord 2 further is wedged, in a manner as above described, between another set of adjacent teeth 43a and 43b so that the pressure of the palatinal stopper 22 is prevented from slackening against the Class III matrix 42, thereby providing an ideal condition for filling the tooth 40a. As above mentioned, the optional variability in diameter of the clamping portion 6, as shown in FIGS. 6A-6C, may permit easier initial wedging between teeth 40a and 40b may minimize patient discomfort in the instance an anesthetic is not permitted or utilized for Class III cavity application.

Accordingly, there is provided the improved dental or clamping cord 2 that may be inserted through or between at least two adjacent teeth 32a, 32b, 40a, 40b, 43a, 43b and thereby, after wedging between the teeth 32, serves to effectively stabilize a dental dam 30 or Class III matrix 42 position.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. A method for retaining a dental dam, comprising:
    positioning a dental dam over and around the teeth in the mouth of a patient;
    selecting a length of a clamping cord, the cord, in a relaxed state, comprised of a core portion of a first diameter and a clamping portion of a second diameter greater than the first diameter wherein the clamping portion comprises fibers arranged longitudinally along and outward of a section of the core portion, the fibers having interstices therebetween, the clamping portion further including a polymeric material substantially surrounding the fibers and filling the interstices;
    inserting the core portion of the clamping cord in a space between two adjacent teeth and proximate a surface of the dental dam; and
    moving the clamp cord axially through the space until the clamping portion becomes lodged in the space between the two adjacent teeth and proximate the surface of the dental dam, thereby prohibiting removal of the dental dam.

2. The method of claim 1 further including cutting the clamping portion at a location outward from the space.

3. A method for retaining a Class III matrix, comprising:
    positioning a Class III matrix about a tooth in the mouth of a patient;
    selecting a length of a clamping cord, the cord, in a relaxed state, comprised of a core portion of a first diameter and a clamping portion of a second diameter greater than the first diameter wherein the clamping portion comprises fibers arranged longitudinally along and outward of a section of the core portion, the fibers having interstices therebetween, the clamping portion further including a polymeric material substantially surrounding the fibers and filling the interstices;
    inserting the core portion of the clamping cord in a space between the Class III matrix and an adjacent tooth; and
    moving the clamp cord axially through the space until the clamping portion becomes lodged in the space between the Class III matrix and the adjacent tooth, thereby prohibiting removal of the Class III matrix.

4. The method of claim 3 wherein the Class III matrix is a mylar foil.

5. The method of claim 3 further including cutting the clamping portion at a location outward from the space.

6. The method of claim 3 wherein the clamping cord further includes a palatinal stopper affixed to an end of the clamping portion opposite the core portion.

7. The method of claim 6 wherein the second diameter of the clamping portion is at a lesser diameter proximal the core portion than proximal the palatinal stopper.

8. The method of claim 6 further including moving the clamp cord axially through the space until the clamping portion becomes lodged in the space between the Class III matrix and the adjacent tooth and wherein the palatinal stopper abuts against the Class III matrix, thereby prohibiting removal of the Class III matrix.

9. The method of claim 8 further including inserting the core portion of the clamping cord in a space between two adjacent teeth and moving the clamp cord axially through the space until the clamping portion becomes lodged in the space between the two adjacent teeth to limit movement of the palatinal stopper away from the Class III matrix.

10. A dental cord, comprising:
a core portion of a first diameter including longitudinally arranged fibers;
a clamping portion of a second diameter greater than the first diameter wherein the clamping portion comprises a portion of the fibers arranged longitudinally along and outward of a section of the core portion, the fibers having interstices therebetween, the clamping portion further including a polymeric material substantially surrounding the fibers and filling the interstices; and
a palatinal stopper being affixed to an end of the clamping portion opposite the core portion.

11. The dental cord of claim 10 wherein the fibers include one of nylon, polyester, polypropylene, and natural fibers.

12. The dental cord of claim 10 wherein the polymeric material includes one of a silicone, thermoplastic elastomer, or polyurethane.

13. The dental cord of claim 10 wherein the first diameter of the core portion is about 0.1 to 0.5 mm.

14. The dental core of claim 10 wherein the second diameter of the clamping portion is about 0.5 to 5.0 mm.

15. The dental cord of claim 10 wherein the clamping portion includes a hardness of about 10 to 90 Shore A.

16. The dental cord of claim 10 wherein the palatinal stopper includes a net component and a polymeric-shaped component, the polymeric component secured to the net component, the net component being affixed to the end of the clamping portion intermediate the polymeric-shaped component and clamping portion.

17. The dental cord of claim 10 wherein the core portion is round or polygonal in shape.

18. The dental cord of claim 10 wherein the clamping portion is round or polygonal in shape.

* * * * *